(12) United States Patent
Bakala et al.

(10) Patent No.: US 7,235,532 B2
(45) Date of Patent: Jun. 26, 2007

(54) ANGIOGENIC AGENTS AND THEIR USES

(75) Inventors: Joanna Bakala, Paris (FR); Jean-Paul Pierre Potier, Paris (FR); Françoise Lawrence, Boullay-lès-Troux (FR); Nathalie Cheviron, Massy (FR); Jérôme Bignon, Neuilly sur Marne (FR); Yves Fromes, Paris (FR)

(73) Assignee: Centre National de la Recherche Scientfique, Paris Cedex (FR)

( * ) Notice: Subject to any disclaimer, the term of this patent is extended or adjusted under 35 U.S.C. 154(b) by 515 days.

(21) Appl. No.: 10/380,983

(22) PCT Filed: Sep. 20, 2001

(86) PCT No.: PCT/FR01/02923
§ 371 (c)(1),
(2), (4) Date: Jul. 29, 2003

(87) PCT Pub. No.: WO02/24218
PCT Pub. Date: Mar. 28, 2002

(65) Prior Publication Data
US 2004/0038907 A1    Feb. 26, 2004

(30) Foreign Application Priority Data
Sep. 21, 2000   (FR) ................... 00 12028

(51) Int. Cl.
*A61K 38/06* (2006.01)
*A61K 38/07* (2006.01)
(52) U.S. Cl. .......... 514/18; 530/330; 530/331
(58) Field of Classification Search .............. None
See application file for complete search history.

(56) References Cited

U.S. PATENT DOCUMENTS

| | | | | |
|---|---|---|---|---|
| 5,470,831 A | | 11/1995 | Whitman et al. | 514/16 |
| 5,589,461 A | * | 12/1996 | Ruhenstroth-Bauer | 514/18 |
| 6,815,426 B2 | * | 11/2004 | Scialdone et al. | 514/18 |

FOREIGN PATENT DOCUMENTS

| | | |
|---|---|---|
| WO | WO97/28183 | 8/1997 |
| WO | WO00/06190 | 2/2000 |

OTHER PUBLICATIONS

Huff, T. et al, ".beta.-Thymosins, small acidic peptides with multiple functions," The International Journal of Biochemistry & Cell Biology, vol. 33, No. 3, 2001, pp. 205-220.

* cited by examiner

*Primary Examiner*—Jeffrey Edwin Russel
(74) *Attorney, Agent, or Firm*—Steptoe & Johnson LLP

(57) ABSTRACT

The present invention relates to the use of a compound of formula I:

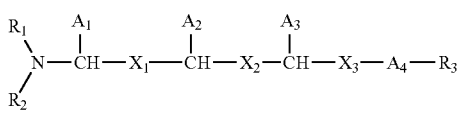

Figure 1A:
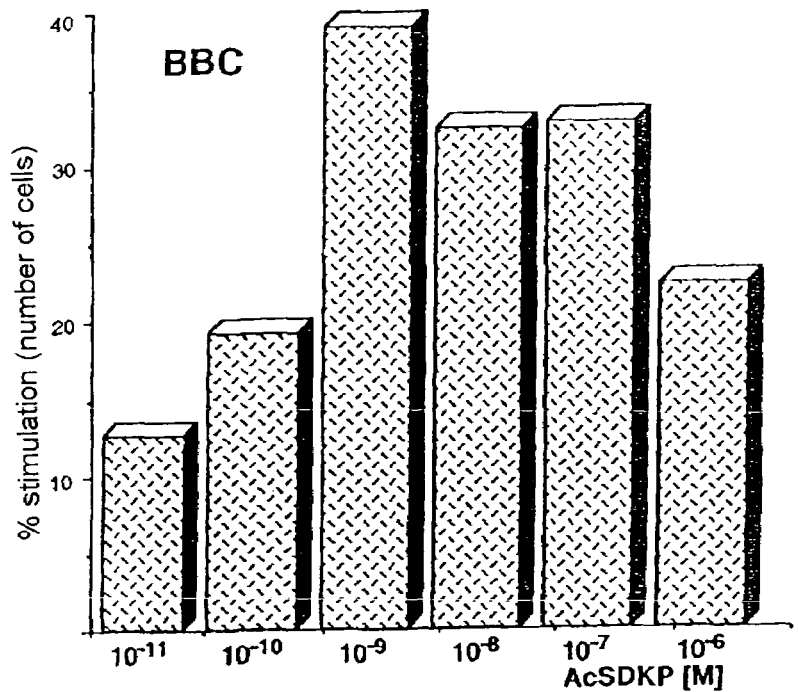

in which, $A_1$ is the radical corresponding to D- or L-Ser,
$A_2$ is the radical corresponding to D- or L-Asp or Glu,
$A_3$ is the radical corresponding to D- or L-Lys, Arg or Gm,
$A_4$ is the radical corresponding to D- or L-Pro,
$R_1$ and $R_2$ are chosen, independently, from H, $C_1$–$C_{12}$-alkyl which may or may not be substituted, $C_7$–$C_{20}$-arylalkyl which may or may not be substituted, $R_4CO$ or $R_4COO$, $R_4$ being $C_1$–$C_{12}$-alkyl which may or may not be substituted, or $C_7$–$C_{20}$-arylalkyl which may or may not be substituted;
among the substitutions, mention should be made of OH, $NH_2$ or COOH,
$X_1$ and $X_2$ are peptide or pseudopeptide bonds,
$X_3$ is CO or $CH_2$ and
$R_3$ is OH, $NH_2$, $C_1$–$C_1$-alkoxy or $NH$-$X_4$-$CH_2$-Z, $X_4$ is a normal or branched $C_1$–$C_{12}$ hydrocarbon, and Z is H, OH, $CO_2H$ or $CONH_2$,
or the corresponding tripeptides comprising the radicals $A_1$, $A_2$, $A_3$,
and also the pharmacautically acceptable salts, for the preparation of a medicament for treating pathologies which may benefit from stimulation of angiogenesis.

17 Claims, 3 Drawing Sheets

Figure 2a
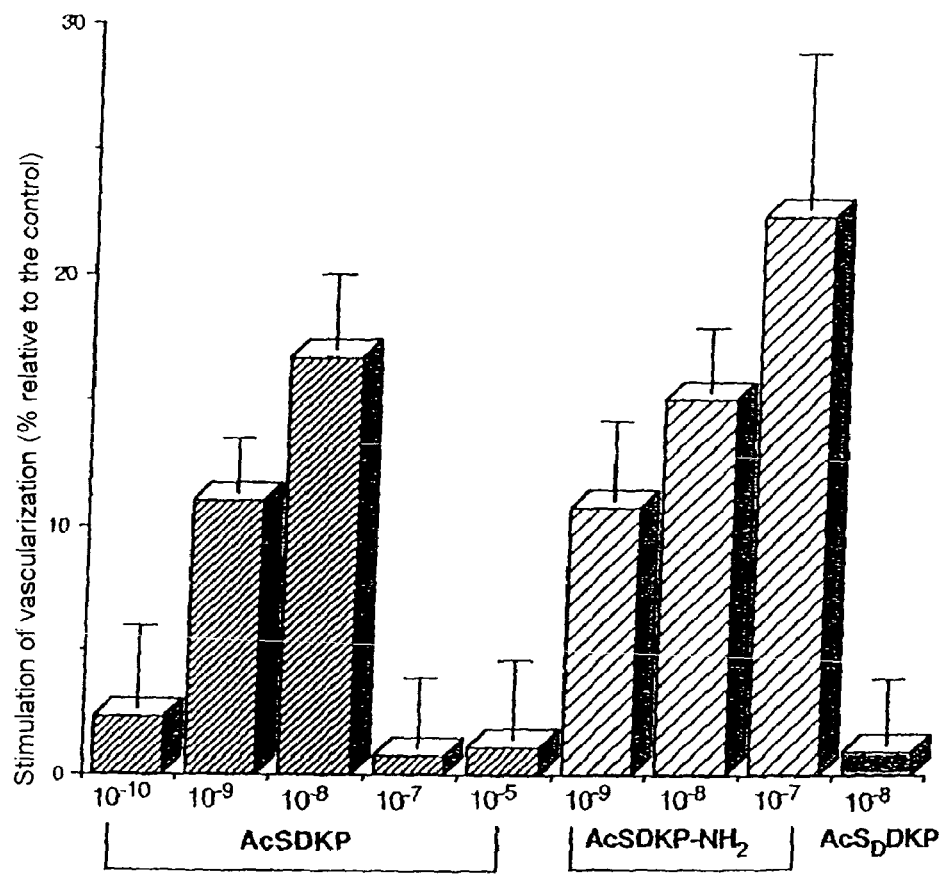
Figure 2b
Figure 2c
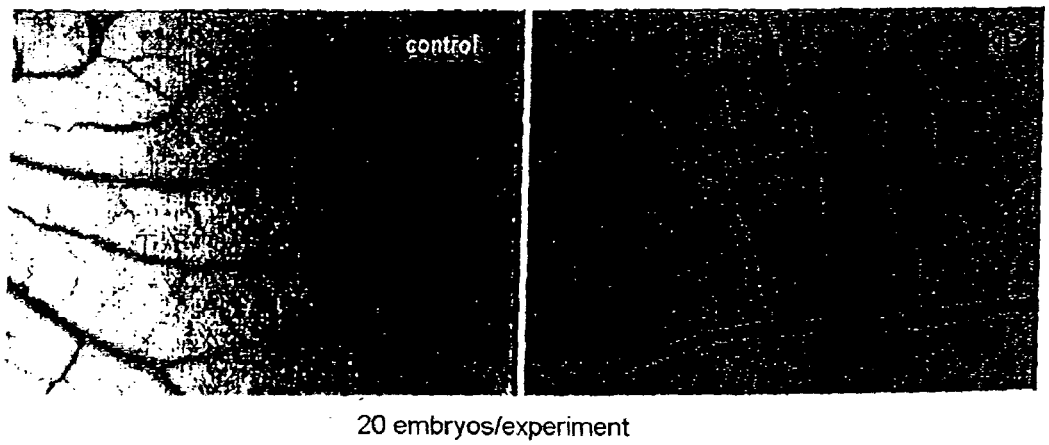
20 embryos/experiment

SEQUENCE LISTING

```
<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ser

<400> SEQUENCE: 1

Ser Asp Lys Pro
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
```

```
<400> SEQUENCE: 2

Ser Asp Lys Pro
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: BINDING
<222> LOCATION: (1)..(2)
<223> OTHER INFORMATION: CH2NH bond

<400> SEQUENCE: 3

Ser Asp Lys Pro
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: BINDING
<222> LOCATION: (2)..(3)
<223> OTHER INFORMATION: CH2NH bond

<400> SEQUENCE: 4

Ser Asp Lys Pro
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: BINDING
<222> LOCATION: (3)..(4)
<223> OTHER INFORMATION: CH2N bond

<400> SEQUENCE: 5

Ser Asp Lys Pro
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: BINDING
<222> LOCATION: (1)..(2)
<223> OTHER INFORMATION: CH2NH bond
<220> FEATURE:
<223> OTHER INFORMATION: C-term amidated

<400> SEQUENCE: 6

Ser Asp Lys Pro
 1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: BINDING
<222> LOCATION: (2)..(3)
<223> OTHER INFORMATION: CH2NH bond
<220> FEATURE:
<223> OTHER INFORMATION: C-term amidated

<400> SEQUENCE: 7

Ser Asp Lys Pro
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: BINDING
<222> LOCATION: (3)..(4)
<223> OTHER INFORMATION: CH2N bond
<220> FEATURE:
<223> OTHER INFORMATION: C-term amidated

<400> SEQUENCE: 8

Ser Asp Lys Pro
 1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: BINDING
```

```
<222> LOCATION: (1)..(2)
<223> OTHER INFORMATION: CH2NH bond

<400> SEQUENCE: 9

Ser Asp Lys Pro
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: BINDING
<222> LOCATION: (2)..(3)
<223> OTHER INFORMATION: CH2NH bond

<400> SEQUENCE: 10

Ser Asp Lys Pro
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: BINDING
<222> LOCATION: (3)..(4)
<223> OTHER INFORMATION: CH2N bond

<400> SEQUENCE: 11

Ser Asp Lys Pro
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: BINDING
<222> LOCATION: (1)..(2)
<223> OTHER INFORMATION: CH2NH bond

<400> SEQUENCE: 12

Ser Asp Lys Pro
 1

<210> SEQ ID NO 13
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: BINDING
<222> LOCATION: (2)..(3)
<223> OTHER INFORMATION: CH2NH bond

<400> SEQUENCE: 13

Ser Asp Lys Pro
  1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: BINDING
<222> LOCATION: (3)..(4)
<223> OTHER INFORMATION: CH2N bond

<400> SEQUENCE: 14

Ser Asp Lys Pro
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: BINDING
<222> LOCATION: (1)..(2)
<223> OTHER INFORMATION: CH2NH bond
<220> FEATURE:
<223> OTHER INFORMATION: C-term amidated

<400> SEQUENCE: 15

Ser Asp Lys Pro
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: BINDING
<222> LOCATION: (2)..(3)
<223> OTHER INFORMATION: CH2NH bond
```

```
<220> FEATURE:
<223> OTHER INFORMATION: C-term amidated

<400> SEQUENCE: 16

Ser Asp Lys Pro
 1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: BINDING
<222> LOCATION: (3)..(4)
<223> OTHER INFORMATION: CH2N bond
<220> FEATURE:
<223> OTHER INFORMATION: C-term amidated

<400> SEQUENCE: 17

Ser Asp Lys Pro
 1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: BINDING
<222> LOCATION: (1)..(2)
<223> OTHER INFORMATION: CH2NH bond
<220> FEATURE:
<223> OTHER INFORMATION: C-term amidated

<400> SEQUENCE: 18

Ser Asp Lys Pro
 1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: BINDING
<222> LOCATION: (2)..(3)
<223> OTHER INFORMATION: CH2NH bond
<220> FEATURE:
<223> OTHER INFORMATION: C-term amidated

<400> SEQUENCE: 19

Ser Asp Lys Pro
 1
```

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: BINDING
<222> LOCATION: (3)..(4)
<223> OTHER INFORMATION: CH2N bond
<220> FEATURE:
<223> OTHER INFORMATION: C-term amidated

<400> SEQUENCE: 20

Ser Asp Lys Pro
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<223> OTHER INFORMATION: C-term amidated

<400> SEQUENCE: 21

Ser Asp Lys Pro
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<223> OTHER INFORMATION: C-term amidated

<400> SEQUENCE: 22

Ser Asp Lys Pro
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: CH3CO-Ser
<220> FEATURE:
<221> NAME/KEY: MOD_RES

```
<222> LOCATION: (4)
<223> OTHER INFORMATION: Pro-NHCH3

<400> SEQUENCE: 23

Ser Asp Lys Pro
  1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: H-Ser
<220> FEATURE:
<221> NAME/KEY: MOD_RES
<222> LOCATION: (4)
<223> OTHER INFORMATION: Pro-NHCH3

<400> SEQUENCE: 24

Ser Asp Lys Pro
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<221> NAME/KEY: MOD_RES
<222> LOCATION: (4)
<223> OTHER INFORMATION: Pro-NHCH3

<400> SEQUENCE: 25

Ser Asp Lys Pro
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: HOOCCH2CH2CO-Ser
<220> FEATURE:
<223> OTHER INFORMATION: C-term amidated

<400> SEQUENCE: 26

Ser Asp Lys Pro
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
    peptide
<220> FEATURE:
<221> NAME/KEY: MOD_RES
<222> LOCATION: (1)
<223> OTHER INFORMATION: Ac-Ser
<220> FEATURE:
<223> OTHER INFORMATION: C-term amidated

<400> SEQUENCE: 27

Ser Asp Lys Pro
  1
```

ANGIOGENIC AGENTS AND THEIR USES

The present invention relates to compounds which induce angiogenesis and to uses thereof, in particular in the treatment of certain vascular pathologies.

Angiogenesis is a fundamental physiological phenomenon which is present throughout the life of an individual and which makes it possible to maintain the structural and functional integrity of the organism. Angiogenesis appears in response to local stimuli which induce a cascade of events leading to the formation of new blood vessels from pre-existing vessels.

During neovascularization, endothelial cells represent the central element essential to the creation of new vessels. Their development and growth are regulated by positive (angiogenic) and negative (angiostatic) factors. In the vessels already formed, the endothelial cells are in the quiescent state. However, in response to an angiogenic stimulus, these cells begin to proliferate and to migrate towards the site of creation of new vessels, which requires the creation of interactions with the surrounding cells and with the elements of the extracellular matrix.

In adults, angiogenesis is a key process of reproductive functions (formation of the yellow body, formation of the placenta, development of the endometrium) and especially of tissue repair during traumas (cicatrization) and ischaemias. It is therefore evident that stimulating angiogenesis by administrating exogenous molecules would represent considerable progress in the therapy of certain ailments, such as the repair of skin, bone, gastric or ophthalmic wounds, for example. Perspectives for clinical use of such angiogenic mediators are also opened up for promoting tissue regeneration associated with ischaemic pathologies or for endothelialization of prostheses.

Several angiogenic factors capable of inducing, in vitro as in vivo, the steps of angiogenesis have been identified (angiogenin, angiopoietin, interleukin 8 (IL-8), epidermal growth factor (EGF), fibroblast growth factors (FGFs), transforming growth factor (TGF) α and β, hepatocyte growth factor (HGF), platelet-derived endothelial growth factor (PDGF), tumour necrosis factor α (TNFα), vascular endothelial growth factors (VEGFs) and placental growth factor (PlGF). All these factors, which are protein in nature, are the subject of intense research on their abilities to repair tissue in humans. Phase I and II clinical trials with VEGFs and FGFs have been started. In particular, these factors are assessed for their therapeutic effects on both cardiac and cerebral ischaemic pathologies. The current results from these trials show that, whatever the method of administration of these factors (infusion of recombinant proteins or gene therapy), the latter do not show the expected therapeutic effectiveness (Ferrara N. Alitalo K., 1999 Clinical applications of angiogenic growth factors and their inhibitors. *Nature Med.*, 5: 1359–1364). New approaches aimed at stimulating tissue neo-vascularization are currently being directed towards therapies which combine several angiogenic factors.

The availability of the angiogenic factors in the form of recombinant proteins has made it possible to show that their local application may accelerate wound healing. The product which appears to be the most advantageous is TGFβ. Its cicatrizing properties have been solidly established for several years and clinical trials are ongoing.

In any event, most of these angiogenic factors are high molecular weight proteins which can only be obtained via the recombinant approach, which, by the same token, increases the cost price of the treatment.

While some polypeptides are capable of stimulating angiogenesis, the inventors have succeeded in demonstrating a real angiogenic activity of peptide structures of small size, and more especially of four amino acids.

It will be noted that the peptides of small size, including formula I or at least the three amino acids (comprising the radicals corresponding to $A_1$, $A_2$, $A_3$), are also part of the invention.

For this reason, the present invention relates, for this type of application, to the use of small peptides, the chemical synthesis of which poses no problem and the cost price of which is quite low.

In addition, the use of these peptides has, from an industrial point of view, a certain number of advantages, among which is, in particular, the fact that they are easier to handle than proteins.

The present invention relates to the use of a compound of formula I:

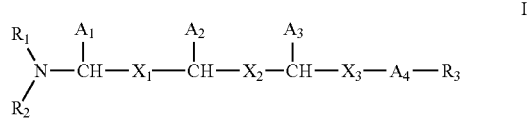

in which, $A_1$ is the radical corresponding to D- or L-Ser,
$A_2$ is the radical corresponding to D- or L-Asp or Glu,
$A_3$ is the radical corresponding to D- or L-Lys, Arg or Orn,
$A_4$ is the radical corresponding to D- or L-Pro,
$R_1$ and $R_2$ are chosen, independently, from H, $C_1$–$C_{12}$-alkyl which may or may not be substituted, $C_7$–$C_{20}$-arylalkyl which may or may not be substituted, $R_4$CO or $R_4$COO, $R_4$ being $C_1$–$C_{12}$-alkyl which may or may not be substituted, or $C_7$–$C_{20}$-arylalkyl which may or may not be substituted;
among the substitutions, mention should be made of OH, $NH_2$ or COOH,
$X_1$ and $X_2$ are peptide or pseudopeptide bonds,
$X_3$ is CO or $CH_2$ and
$R_3$ is OH, $NH_2$, $C_1$–$C_{12}$-alkoxy or NH—$X_4$—$CH_2$—Z, $X_4$ is a normal or branched $C_1$–$C_{12}$ hydrocarbon, and Z is H, OH, $CO_2$H or $CONH_2$, or the corresponding tripeptides comprising the radicals $A_1$, $A_2$, $A_3$, and also the pharmaceutically acceptable salts, for the preparation of a medicament for treating pathologies which may benefit from angiogensis.

The expression "benefit from angiogenesis" is intended to mean benefit from an induction and/or from a stimulation of angiogenesis.

The peptides or pseudopeptides corresponding to these formulae are derived from the basic structure of the tetrapeptide acetyl-Ser-Asp-Lys-Pro (AcSDKP) (SEQ ID NO: 1), these derivatives being intended, in particular, to increase the angiogenic activity, to decrease the side effects and/or to increase the lifetime in physiological medium.

Among the compounds of the invention, mention should be made of the tripeptide derived from a peptide AcSDKP (SEQ ID NO: 1) and comprising the radicals $A_1$, $A_2$, $A_3$.

The basic structure is a molecule which has been isolated from foetal calf bone marrow and the uses of which have, until now, been linked to a function of inhibiting haematopoietic stem cell proliferation, described in particular in WO 88/00594.

The expression "radical corresponding to" should be taken to mean the radical A of the formula: $NH_2$—CH(A)—COOH corresponding to the amino acid.

Thus, A is

—$CH_2$OH for Ser,
—$CH_2$COOH for Asp,

—$CH_2$—$CH_2$—COOH for Glu,
—$(CH_2)_3$—NH—C(NH)$NH_2$ for Arg,
—$(CH_2)_3$—$NH_2$ for Orn and
—$(CH_2)_4$—$NH_2$ for Lys, for the terminal amino acid $A_4$, it is either the structure:
=N—CH(A)-CO— or NH—(CH)A-CO—.

The term "pseudopeptide" is intended to denote compounds similar to the reference peptides but in which one or more peptide bonds —CO—NH— have been replaced with a bond equivalent to the peptide bond, which is termed pseudopeptide, i.e. —$CH_2$—NH—, —$CH_2$—S—, —$CH_2$—O—, —CO—$CH_2$—, —$CH_2$—CO—, —$CH_2$—$CH_2$—, represented by ψ($CH_2$NH) for example.

Among the radicals $R_1$ and $R_2$, preference will be given more particularly to the radicals: H and $(C_1-C_3)$-alkyl-CO—, in particular $CH_3$CO and also HOOC—$CH_2$—$CH_2$—CO—O.

Similarly, $R_3$ is preferably $NH_2$, OH or $NHCH_3$.

Among the compounds, mention should be made of:
$CH_3$CO-Ser-Asp-Lys-Pro-OH (SEQ ID NO: 2)
$CH_3$CO-Ser-ψ-($CH_2$NH)-Asp-Lys-Pro-OH (SEQ ID NO: 3)
$CH_3$CO-Ser-Asp-ψ-($CH_2$NH)-Lys-Pro-OH (SEQ ID NO: 4)
$CH_3$CO-Ser-Asp-Lys-ψ-($CH_2$N)-Pro-OH (SEQ ID NO: 5)
$CH_3$CO-Ser-ψ-($CH_2$NH)-Asp-Lys-Pro-$NH_2$ (SEQ ID NO: 6)
$CH_3$CO-Ser-Asp-ψ-($CH_2$NH)-Lys-Pro-$NH_2$ (SEQ ID NO: 7)
$CH_3$CO-Ser-Asp-Lys-ψ-($CH_2$N)-Pro-$NH_2$ (SEQ ID NO: 8)
H-Ser-ψ-($CH_2$NH)-Asp-Lys-Pro-OH (SEQ ID NO: 9)
H-Ser-Asp-ψ-($CH_2$NH)-Lys-Pro-OH (SEQ ID NO: 10)
H-Ser-Asp-Lys-ψ-($CH_2$N)-Pro-OH (SEQ ID NO: 11)
HOOC$CH_2CH_2$CO-Ser-ψ-($CH_2$NH)-Asp-Lys-Pro-OH (SEQ ID NO: 12)
HOOC$CH_2CH_2$CO-Ser-Asp-ψ-($CH_2$NH)-Lys-Pro-OH (SEQ ID NO: 13)
HOOC$CH_2CH_2$CO-Ser-Asp-Lys-ψ-($CH_2$N)-Pro-OH (SEQ ID NO: 14)
H-Ser-ψ-($CH_2$NH)-Asp-Lys-Pro-$NH_2$ (SEQ ID NO: 15)
H-Ser-Asp-ψ-($CH_2$NH)-Lys-Pro-$NH_2$ (SEQ ID NO: 16)
H-Ser-Asp-Lys-ψ-($CH_2$N)-Pro-$NH_2$ (SEQ ID NO: 17)
HOOC$CH_2CH_2$CO-Ser-ψ-($CH_2$NH)-Asp-Lys-Pro-$NH_2$ (SEQ ID NO: 18)
HOOC$CH_2CH_2$CO-Ser-Asp-ψ-($CH_2$NH)-Lys-Pro-$NH_2$ (SEQ ID NO: 19)
HOOC$CH_2CH_2$CO-Ser-Asp-Lys-ψ-($CH_2$N)-Pro-$NH_2$ (SEQ ID NO: 20)
$CH_3$CO-Ser-Asp-Lys-Pro-$NH_2$ (SEQ ID NO: 21)
H-Ser-Asp-Lys-Pro-$NH_2$ (SEQ ID NO: 22)
$CH_3$CO-Ser-Asp-Lys-Pro-$NHCH_3$ (SEQ ID NO: 23)
H-Ser-Asp-Lys-Pro-$NHCH_3$ (SEQ ID NO: 24)
HOOC$CH_2CH_2$CO-Ser-Asp-Lys-Pro-$NHCH_3$ (SEQ ID NO: 25)
HOOC$CH_2CH_2$CO-Ser-Asp-Lys-Pro-$NH_2$. (SEQ ID NO: 26)

The following compounds should also be mentioned:
$CH_3$CO-Ser-Asp-Lys-OH
$CH_3$CO-Ser-ψ-($CH_2$NH)-Asp-Lys-OH
$CH_3$CO-Ser-Asp-ψ-($CH_2$NH)-Lys-OH
$CH_3$CO-Ser-ψ-($CH_2$NH)-Asp-Lys-$NH_2$
$CH_3$CO-Ser-Asp-ψ-($CH_2$NH)-Lys-$NH_2$
H-Ser-ψ-($CH_2$NH)-Asp-Lys-OH
H-Ser-Asp-ψ-($CH_2$NH)-Lys-OH
HOOC$CH_2CH_2$CO-Ser-ψ-($CH_2$NH)-Asp-Lys-OH
HOOC$CH_2CH_2$CO-Ser-Asp-ψ-($CH_2$NH)-Lys-OH
H-Ser-ψ-($CH_2$NH)-Asp-Lys-$NH_2$
H-Ser-Asp-ψ-($CH_2$NH)-Lys-$NH_2$
HOOC$CH_2CH_2$CO-Ser-ψ-($CH_2$NH)-Asp-Lys-$NH_2$
HOOC$CH_2CH_2$CO-Ser-Asp-ψ-($CH_2$NH)-Lys-$NH_2$
$CH_3$CO-Ser-Asp-Lys-$NH_2$
H-Ser-Asp-Lys-$NH_2$
$CH_3$CO-Ser-Asp-Lys-$NHCH_3$
H-Ser-Asp-Lys-$NHCH_3$
HOOC$CH_2CH_2$CO-Ser-Asp-Lys-$NHCH_3$
HOOC$CH_2CH_2$CO-Ser-Asp-Lys-$NH_2$ Among the pharmaceutically acceptable salts, mention should be made in particular of the salts with inorganic acids; chloride, sulphate, phosphate, nitrate, hydrochlorate, but also with organic acids; in particular lactate, citrate for example, and also the salts with bases.

The inventors have now demonstrated that this tetrapeptide, or related peptides of formula I, are capable of inducing angiogenesis.

Among the treatments for pathologies which may benefit from stimulation of angiogenesis, mention should be made of vascular pathologies, in particular in the treatment of ischaemias. Thus, the compounds according to the present invention may be used in particular in the following cases:
1. induction of collateral vessel formation in the case of ischaemic pathologies:
   myocardial ischaemia (disease of the coronary arteries, myocardial infarction),
   peripheral ischaemia (occlusion of the peripheral arteries),
   cerebral ischaemias (cerebral vascular diseases),
2. fracture cicatrization and repair in the case of tissue lesions:
   dermatology: burns or injuries, chronic ulcers,
   ophthalmology: corneal or retinal lesions,
   gastroenterology: gastroduodenal ulcers,
   bone surgery: hard tissue repair: bone + cartilage,
3. nerve generation,
4. reconstructive surgery and plastic surgery,
5. endothelialization of vascular implants and bio-materials,
6. organ transplantation (for example islets of Langherans).

The above list constitutes only some of the possible applications, in particular in the case of combined treatments; acceleration of angiogenesis may make it possible to accelerate healing.

The compounds according to the present invention are also useful in ex vivo or in vitro tissue cultures requiring neovascularization, as angiogenesis inducers, for example, in the culturing of skin or in the coating of materials with tissues.

It has been possible, in vitro, to show that AcSDKP (SEQ ID NO: 1) is capable of significantly stimulating the growth of human endothelial cells (HUVEC and EA.hy926) and of endothelial cells originating from bovine brain capillaries (BBC).

In vivo, the angiogenic activity of AcSDKP (SEQ ID NO: 1) has been tested on the "chick embryo chorioallantoic membrane" experimental model. On this model, AcSDKP (SEQ ID NO: 1) induces neovascularization considerably.

In addition, a preliminary study carried out on medullar cells has revealed that, in vitro, AcSDKP (SEQ ID NO: 1) increases the adhesion of these cells to various components of the extracellular matrix, such as fibronectin, collagen IV and laminin. Comparable results have been obtained in a preliminary experiment carried out with HUVEC human endothelial cells. It is clearly established that these interactions between endothelial cells and the extracellular matrix are determinant for the neovascularization and are involved at various steps of angiogenesis. Specifically, the extracellular matrix influences the proliferation and the migration of vascular endothelial cells, and also their ability to differentiate and to organize into capillaries in order to form new functional vessels suited to their tissue microenvironment.

The compounds according to the present invention may be administered in a suitable pharmaceutical form, for example via the oral, intravenous, transdermal, pulmonary, subcutaneous, nasal or other route, with the corresponding forms, whether they are tablets, injectable solutions, or ointments or gels, in particular when the preparation of compositions intended to improve cicatrization is desired.

In the case of revascularization, in particular in the treatment of ischaemias, use will preferably be made of injectable routes, and in particular of infusions.

Of course, the compounds according to the present invention may be used in combination with other active principles possibly intended to treat the pathology directly, when the angiogenesis will only constitute a support therapy for a main therapy, for example in the treatment of gastroduodenal ulcers.

With regard to the administration doses, in the models used, it has been noted that the angiogenic effect reaches a maximum and then decreases again if the doses administered are not increased. The administration dose will therefore possibly have to be adjusted to suit the type of pathology and to suit the patient, if necessary. The optimum doses of AcSDKP (SEQ ID NO: 1) are between $10^{-5}$ and $10^{-11}$ M and will preferably be between $10^{-6}$ and $10^{-9}$.

The compounds according to the present invention may be synthesized using synthetic processes of the peptide or pseudopeptide type, in particular the processes described in WO 88/00594, which describes the synthesis of the AcSDKP (SEQ ID NO: 1) derivative, and in patent WO 97/28183, which describes the synthesis of pseudopeptides relating to AcSDKP (SEQ ID NO: 1).

LEGENDS TO THE FIGURES

Figure 1B:
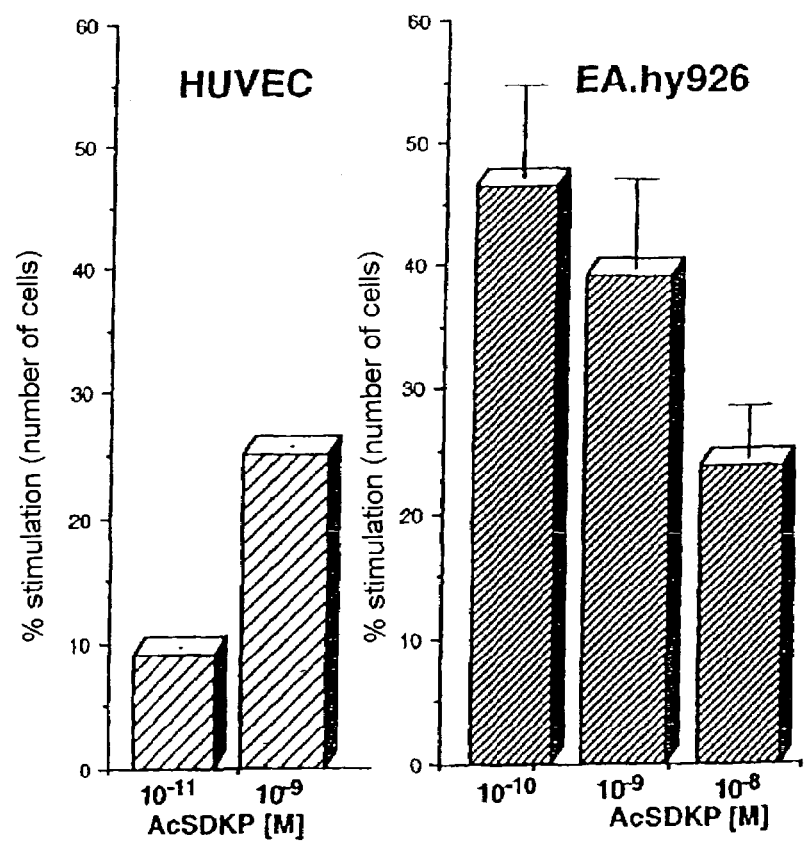

FIGS. 1a, 1b and 1c: AcSDKP (SEQ ID NO: 1) stimulates the growth of bovine (BBC) and human (HUVEC and EA.hy926) endothelial cells, in vitro.

FIGS. 2a, 2b and 2c: Effect of AcSDKP (SEQ ID NO: 1) and of analogues thereof on the vascularization of the chick embryo chorioallantoic membrane (CAM). FIG. 2A discloses SEQ ID NOS: 1 and 27, respectively, in order of appearance.

Figure 3:
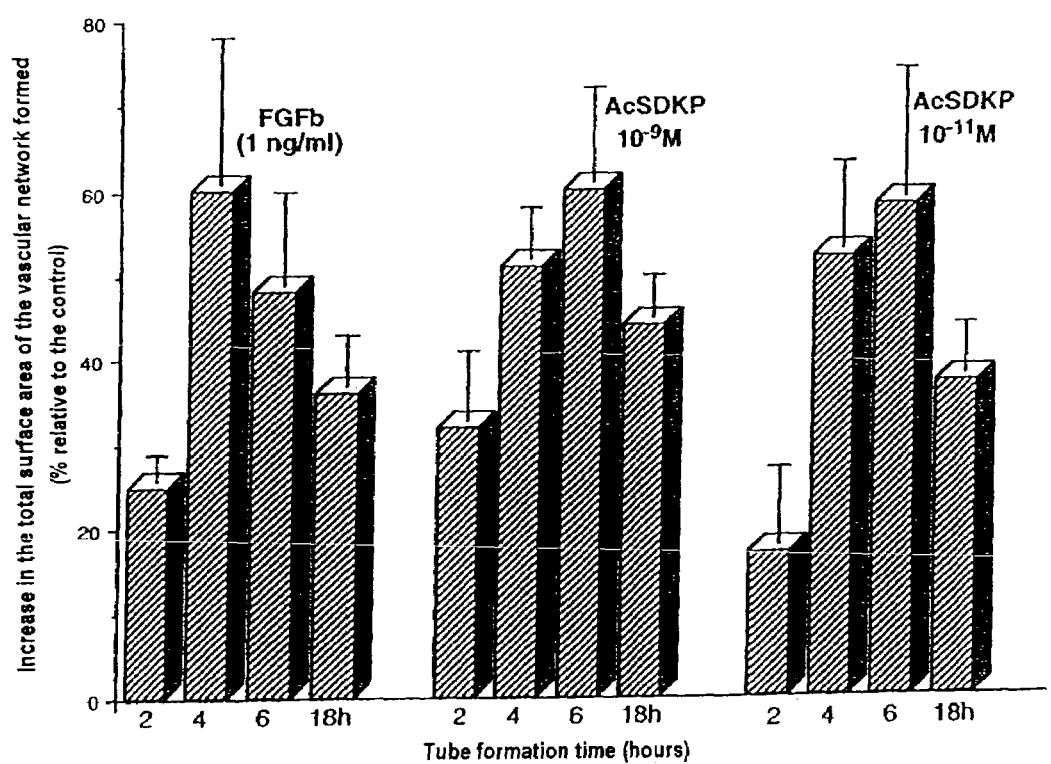

FIG. 3: Effect of AcSDKP (SEQ ID NO: 1) on the formation of vascular tubes, in vitro, by endothelial cells (EA.hy926) in Matrigel.

EXAMPLE 1

The following tests were carried out with the tetrapeptide AcSDKP (SEQ ID NO: 1); the following results were observed:

AcSDKP (SEQ ID NO: 1) significantly stimulates the growth of endothelial cells originating from bovine brain capillaries (BBC) and of human umbilical cord vein endothelial cells (HUVEC), and also the growth of an immortalized HUVEC cell line (EA.hy926). The mitogenic effect of AcSDKP (SEQ ID NO: 1) manifests itself at concentrations ranging between $10^{-6}$ and $10^{-11}$ M, with a maximum for $10^{-9}$ M.

The results of these studies are given in FIGS. 1a, 1b and 1c.

An additional study carried out on total marrow (containing, inter alia, endothelial cells) showed that, in vitro, AcSDKP (SEQ ID NO: 1) increases the adhesion of the marrow cells to diverse components of the extracellular matrix, such as fibronectin, collagen IV and laminin.

The optimum concentration of AcSDKP (SEQ ID NO: 1) in this type of model is between $10^{-6}$ and $10^{-8}$ M.

Comparable results were obtained in preliminary experiments carried out on HUVEC human endothelial cells.

It is well established that these interactions between endothelial cells and the extracellular matrix are determinant for the neovascularization and are involved at various steps of angiogenesis. Specifically, the extracellular matrix influences the proliferation and migration of vascular endothelial cells, and also their ability to differentiate and to organize into capillaries in order to form new functional vessels suitable for their tissue microenvironment.

EXAMPLE 2

The following experiments were carried out on the chick embryo chorioallantoic membrane experimental model and the activity of AcSDKP (SEQ ID NO: 1) and of analogues thereof was tested on this model. It was possible to demonstrate that AcSDKP (SEQ ID NO: 1) and its proteolysis-resistant analogue, AcSDKP-NH$_2$ (SEQ ID NO: 27), significantly induced neovascularization, whereas its optical isomer, AcS$_D$DKP, had no angiogenic effect. The increase in the density of vascularization varies depending on the dose studied, with a maximum effect for AcSDKP (SEQ ID NO: 1) and AcSDKP-NH$_2$ (SEQ ID NO: 27) at concentrations of between $10^{-9}$ M and $10^{-7}$ M (FIGS. 2a, 2b and 2c).

EXAMPLE 3

The results of an in vivo study carried out in rats show that AcSDKP (SEQ ID NO: 1) also induces neovascularization in mammals.

In these experiments, AcSDKP (SEQ ID NO: 1) was injected into the abdominal muscle in normal rats (treatment twice a day for 5 hours). An angiography of the abdominal walls carried out in the animal sacrificed on day 8 revealed a more developed vascularization (significant increase in the number of small vessels) in animals treated with AcSDKP (SEQ ID NO: 1) at the dose of 5 µg/kg/injection. It should be emphasized that this effect remains over time (observations made one month after the start of treatment). No significant modification of the vascularization was observed following administration of AcSDKP (SEQ ID NO: 1) at the dose of 50 µg/kg/injection.

The loss of the angiogenic activity of AcSDKP (SEQ ID NO: 1) linked with the increase in the dose administered, which was observed both in vitro (cells in culture) and in vivo (chick and rat embryo) is in agreement with the existence, for AcSDKP (SEQ ID NO: 1), of a bell-shaped dose-response, as previously described [(Guignon M., Bonnet D, Lemoine F., Kobari L., Parmentier C., Mary J. Y., Najman A. (1990) Inhibition of human bone marrow progenitors by the synthetic tetrapeptide AcSDKP (SEQ ID NO: 1); Exp. Hematol. 18, 1112; Jackson J. D., Yan Y., Ewel C., Talmage J .E. (1996) Activity of Acetyl-Ser-Asp-Lys-Pro (AcSDKP) (SEQ ID NO: 1) on hematopoietic progenitors in short term and long-term murine bone marrow cultures. Exp. HematoL, 24, 475)].

EXAMPLE 4

The organization of the endothelial cells into vascular tubes constitutes an important step of angiogenesis. It was shown that AcSDKP (SEQ ID NO: 1) stimulates, both in vitro and in vivo, the formation of the tubes in Matrigel.

The experiments carried out in vitro with two types of endothelial cell show that AcSDKP (SEQ ID NO: 1), at the concentrations of $10^{-9}$ M and $10^{-11}$ M, induces an increase of the total surface area of the vascular network compared to the control values. The maximum stimulations, corresponding to an increase of 60% and 58%, respectively, were observed after exposure of the cells to the tetrapeptide for 6 hours. These effects are comparable to that generated by FGFb at 1 nglml (FIG. 3).

In vivo, AcSDKP (SEQ ID NO: 1) induces, in a dose-dependent manner, the vascular invasion of Matrigel placed under the skin of the animal (Sprague-Dawley rat). In this experiment, AcSDKP (SEQ ID NO: 1) was mixed with the Matrigel before implantation. Seven days later, the animals were sacrificed and the Matrigel samples were taken and fixed in formol, and were the subject of a histological study. The microscopic observations and the quantification of the vessels after staining and immunolabelling revealed the presence of a much greater number of vessels within the Matrigel having contained AcSDKP (SEQ ID NO: 1) compared to the control Matrigel (Table 1). For the quantification, the vascular sections were counted on 10 consecutive fields (surface area =32 mm$^2$) from the richest zone.

TABLE 1

Effect of AcSDKP on the vascular invasion in vivo of Matrigel

| Treatment | Number of vessels (% increase compared to control) | | |
|---|---|---|---|
| | Exp. 1 | Exp. 2 | Exp. 3 |
| AcSDKP $10^{-5}$ M | 60 | 185 | — |
| AcSDKP $10^{-6}$ M | — | 121 | — |
| AcSDKP $10^{-7}$ M | 294 | 118 | 139 |
| AcSDKP $10^{-8}$ M | — | 223 | — |
| AcSDKP $10^{-9}$ M | 108 | 61 | 197 |
| FGFb (50 ng/ml) | — | 297 | — |

EXAMPLE 5

Given the ability of angiogenic factors to stimulate, in vivo, the formation of new vessels in lesioned regions which are characterized by a deficiency in vascularization, we studied the effectiveness of AcSDKP (SEQ ID NO: 1) in promoting tissue lesion repair, using a skin flap model. In fact, the distal necrosis of skin flaps generally results from rupturing of the vascular network and therefore from an insufficiency of arterial flow, which poses considerable problems in the fields of plastic and reconstructive surgery. It has been proved that administering an angiogenic factor, which contributes to the revascularization of these flaps, thus increases their survival.

We showed that s.c. injections of AcSDKP (SEQ ID NO: 1) into the region of the flaps decreases their necrosis. Pedicled ventral skin flaps (6×6 cm) (left inguinal pedicle) were made in the Sprague-Dawley rats.

AcSDKP (SEQ ID NO: 1) was administered at the dose of 5 μg/kg/ injection (250 μl/injection) immediately after the surgical intervention, and then again 5 times at 12 hour intervals. The results obtained show that the survival of the flaps in the animals treated with AcSDKP (SEO ID NO: 1) increases by 10% compared to the controls. From a macroscopic point of view, the decrease in necrosis is accompanied by the increase in the density of the vascularization over the internal surface of the flaps.

The invention claimed is:

1. A method of inducing angiogenesis in vivo, comprising administering to a patient in need thereof, an angiogenesis inducing effective amount of a compound of formula I:

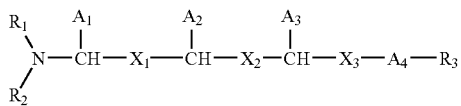

in which the compound of formula I is a tetrapeptide or tripeptide and in which, $A_1$ is $CH_2OH$, $A_2$ is $CH_2COOH$ or $CH_2-CH_2-COOH$, $A_3$ is $(CH_2)_4-NH_2$, $(CH_2)_3-NH-C(NH)NH_2$, or $(CH_2)_3-NH_2$, $A_4$ is a radical corresponding to D- or L-Pro when the compound of formula I is a tetrapeptide, $R_1$ and $R_2$ are independently selected from H, $C_1-C_{12}$-alkyl which may be optionally substituted, $C_7-C_{20}$-arylalkyl which may be optionally substituted, $R_4CO$ or $R_4COO$, $R_4$ being $C_1-C_{12}$-alkyl which may be optionally substituted, or $C_7-C_{20}$-arylalkyl which may be optionally substituted, $X_1$ and $X_2$ are peptide or pseudopeptide bonds, $X_3$ is CO or $CH_2$ when the compound of formula I is a tetrapeptide, or a bond when the compound of formula I is a tripeptide, and $R_3$ is OH, $NH_2$, $C_1-C_{12}$-alkoxy or $NH-X_4-CH_2-Z$, $X_4$ is a straight or branched $C_1-C_{12}$ hydrocarbon, and Z is H, OH, $CO_2H$ or $CONH_2$, or a pharmaceutically acceptable salt thereof.

2. The method according to claim 1, wherein angiogenesis is induced to treat a vascular pathology.

3. The method according to claim 1, wherein angiogenesis is induced to treat a tissue lesion.

4. The method according to claim 1, wherein angiogenesis is induced to aid in nerve regeneration, reconstructive surgery, endothelialization of material or organ transplantation.

5. The method according to claim 1, wherein the compound of formula I is a pseudopeptide derived from a peptide AcSDKP (SEQ ID NO: 1).

6. The method according to claim 1, wherein the compound of formula I is a tripeptide derived from a peptide AcSDKP (SEQ ID NO: 1) and comprising the radicals $A_1$, $A_2$, $A_3$.

7. The method according to claim 1, wherein the compound of formula I is a tetrapeptide which is:

CH$_3$CO-Ser-Asp-Lys-Pro-OH (SEQ ID NO: 2),
CH$_3$CO-Ser-ψ-(CH$_2$NH)-Asp-Lys-Pro-OH (SEQ ID NO: 3),
CH$_3$CO-Ser-Asp-ψ-(CH$_2$NH)-Lys-Pro-OH (SEQ ID NO: 4),
CH$_3$CO-Ser-Asp-Lys-ψ-(CH$_2$N)-Pro-OH (SEQ ID NO: 5),
CH$_3$CO-Ser-ψ-(CH$_2$NH)-Asp-Lys-Pro-NH$_2$ (SEQ ID NO: 6),
CH$_3$CO-Ser-Asp-ψ-(CH$_2$NH)-Lys-Pro-NH$_2$ (SEQ ID NO: 7),
CH$_3$CO-Ser-Asp-Lys-ψ-(CH$_2$N)-Pro-NH$_2$ (SEQ ID NO: 8),
H-Ser-ψ-(CH$_2$NH)-Asp-Lys-Pro-OH (SEQ ID NO: 9),
H-Ser-Asp-ψ-(CH$_2$NH)-Lys-Pro-OH (SEQ ID NO: 10),
H-Ser-Asp-Lys-ψ-(CH$_2$N)-Pro-OH (SEQ ID NO: 11),
HOOCCH$_2$CH$_2$CO-Ser-ψ-(CH$_2$NH)-Asp-Lys-Pro-OH (SEQ ID NO: 12),
HOOCCH$_2$CH$_2$CO-Ser-Asp-ψ-(CH$_2$NH)-Lys-Pro-OH (SEQ ID NO: 13),
HOOCCH$_2$CH$_2$CO-Ser-Asp-Lys-ψ-(CH$_2$N)-Pro-OH (SEQ ID NO: 14),
H-Ser-ψ-(CH$_2$NH)-Asp-Lys-Pro-NH$_2$ (SEQ ID NO: 15),
H-Ser-Asp-ψ-(CH$_2$NH)-Lys-Pro-NH$_2$ (SEQ ID NO: 16),
H-Ser-Asp-Lys-ψ-(CH$_2$N)-Pro-NH$_2$ (SEQ ID NO: 17),
HOOCCH$_2$CH$_2$CO-Ser-ψ-(CH$_2$NH)-Asp-Lys-Pro-NH$_2$ (SEQ ID NO: 18),
HOOCCH$_2$CH$_2$CO-Ser-Asp-ψ-(CH$_2$NH)-Lys-Pro-NH$_2$ (SEQ ID NO: 19),
HOOCCH$_2$CH$_2$CO-Ser-Asp-Lys-ψ-(CH$_2$N)-Pro-NH$_2$ (SEQ ID NO: 20),
CH$_3$CO-Ser-Asp-Lys-Pro-NH$_2$ (SEQ ID NO: 21),
H-Ser-Asp-Lys-Pro-NH$_2$ (SEQ ID NO: 22),
CH$_3$CO-Ser-Asp-Lys-Pro-NHCH$_3$ (SEQ ID NO: 23),
H-Ser-Asp-Lys-Pro-NHCH$_3$ (SEQ ID NO: 24),
HOOCCH$_2$CH$_2$CO-Ser-Asp-Lys-Pro-NHCH$_3$ (SEQ ID NO: 25), or
HOOCCH$_2$CH$_2$CO-Ser-Asp-Lys-Pro-NH$_2$ (SEQ ID NO: 26).

8. The method according to claim 1, wherein the compound of formula I is a tripeptide which is:

CH$_3$CO-Ser-Asp-Lys-OH,
CH$_3$CO-Ser-ψ-(CH$_2$NH)-Asp-Lys-OH,
CH$_3$CO-Ser-Asp-ψ-(CH$_2$NH)-Lys-OH,
CH$_3$CO-Ser-ψ-(CH$_2$NH)-Asp-Lys-NH$_2$,
CH$_3$CO-Ser-Asp-ψ-(CH$_2$NH)-Lys-NH$_2$,
H-Ser-ψ-(CH$_2$NH)-Asp-Lys-OH,
H-Ser-Asp-ψ-(CH$_2$NH)-Lys-OH,
HOOCCH$_2$CH$_2$CO-Ser-ψ-(CH$_2$NH)-Asp-Lys-OH,
HOOCCH$_2$CH$_2$CO-Ser-Asp-ψ-(CH$_2$NH)-Lys-OH,
H-Ser-ψ-(CH$_2$NH)-Asp-Lys-NH$_2$,
H-Ser-Asp-ψ-(CH$_2$NH)-Lys-NH$_2$,
HOOCCH$_2$CH$_2$CO-Ser-ψ-(CH$_2$NH)-Asp-Lys-NH$_2$,

HOOCCH$_2$CH$_2$CO-Ser-Asp-ψ-(CH$_2$NH)-Lys-NH$_2$,
CH$_3$CO-Ser-Asp-Lys-NH$_2$,
H-Ser-Asp-Lys-NH$_2$,
CH$_3$CO-Ser-Asp-Lys-NHCH$_3$,
H-Ser-Asp-Lys-NHCH$_3$,
HOOCCH$_2$CH$_2$CO-Ser-Asp-Lys-NHCH$_3$, or
HOOCCH$_2$CH$_2$CO-Ser-Asp-Lys-NH$_2$.

9. The method of claim 1, wherein the $C_1$–$C_{12}$-alkyl and $C_7$–$C_{20}$-arylalkyl radicals are optionally substituted with OH, NH$_2$ or COOH.

10. The method of claim 2, wherein the vascular pathology is ischaemias.

11. The method of claim 3, wherein the tissue lesion is a fracture cicatrization or repair.

12. The method of claim 1, wherein the pseudopeptide bond is —CH$_2$—NH—, —CH$_2$—S—, —CH$_2$—O—, —CO—CH$_2$—, —CH$_2$—CO, or —CH$_2$—CH$_2$—.

13. The method of claim 1, wherein R$_1$ and R$_2$ are H or ($C_1$–$C_3$)-alkyl-CO—.

14. The method of claim 1, wherein R$_1$ and R$_2$ are CH$_3$CO or HOOC—CH$_2$—CH$_2$—CO—O.

15. The method of claim 1, wherein R$_3$ is NH$_2$, OH or NHCH$_3$.

16. The method of claim 1, wherein the compound of formula I is AcSDKP (SEQ ID NO: 1) and the compound is administered in a dose of 10 μg/kg/day.

17. A method of inducing angiogenesis in vitro, comprising treating a tissue culture with an angiogenesis inducing effective amount of a compound of formula I:

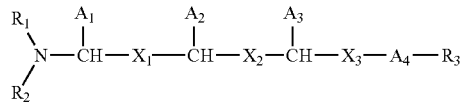

in which the compound of formula I is a tetrapeptide or tripeptide and in which, A$_1$ is CH$_2$OH, A$_2$ is CH$_2$COOH or CH$_2$—CH$_2$—COOH, A$_3$ is (CH$_2$)$_4$—NH$_2$, (CH$_2$)$_3$—NH—C(NH)NH$_2$, or (CH$_2$)$_3$—NH$_2$, A$_4$ is a radical corresponding to D- or L-Pro when the compound of formula I is a tetrapeptide, R$_1$ and R$_2$ are independently selected from H, $C_1$–$C_{12}$-alkyl which may be optionally substituted, $C_7$–$C_{20}$-arylalkyl which may be optionally substituted, R$_4$CO or R$_4$COO, R$_4$ being $C_1$–$C_{12}$-alkyl which may be optionally substituted, or $C_7$–$C_{20}$-arylalkyl which may be optionally substituted, X$_1$ and X$_2$ are peptide or pseudopeptide bonds, X$_3$ is CO or CH$_2$ when the compound of formula I is a tetrapeptide, or a bond when the compound of formula I is a tripeptide, and R$_3$ is OH, NH$_2$, $C_1$–$C_{12}$-alkoxy or NH—X$_4$—CH$_2$-Z, X$_4$ is a straight or branched $C_1$–$C_{12}$ hydrocarbon, and Z is H, OH, CO$_2$H or CONH$_2$, or a pharmaceutically acceptable salt thereof.

* * * * *